(12) United States Patent
Ho et al.

(10) Patent No.: US 6,805,117 B1
(45) Date of Patent: Oct. 19, 2004

(54) UNIVERSAL FITTING HEADGEAR

(75) Inventors: Peter Ho, Pittsburgh, PA (US); Marcel D. Jaffre, Wendel, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 10/283,526

(22) Filed: Oct. 30, 2002

Related U.S. Application Data

(60) Provisional application No. 60/346,163, filed on Nov. 7, 2001.

(51) Int. Cl.[7] ............................. A62B 18/08; A62B 18/00
(52) U.S. Cl. ............................. 128/201.22; 128/201.23; 128/207.17; 128/207.11; 128/206.27
(58) Field of Search ................. 128/201.22, 206.13, 128/206.27, 207.17, 207.11, 204.11, 201.23

(56) References Cited

U.S. PATENT DOCUMENTS

| | | | | |
|---|---|---|---|---|
| 1,395,761 A | * | 11/1921 | Monro et al. | 128/207.11 |
| 1,706,601 A | * | 3/1929 | Drager | 128/207.11 |
| 2,199,690 A | * | 5/1940 | Bullard | 128/207.11 |
| 2,353,643 A | * | 7/1944 | Bulbulian | 128/207.11 |
| 2,974,665 A | * | 3/1961 | Motsinger | 128/201.19 |
| 3,220,408 A | * | 11/1965 | Silverberg | 128/206.23 |
| 3,249,106 A | * | 5/1966 | Motsinger | 128/206.17 |
| 5,038,776 A | | 8/1991 | Harrison et al. | |
| 5,191,882 A | * | 3/1993 | Vogliano | 128/207.11 |
| 5,441,046 A | | 8/1995 | Starr et al. | |
| 5,481,763 A | * | 1/1996 | Brostrom et al. | 2/452 |
| 5,517,986 A | | 5/1996 | Starr et al. | |
| 5,542,128 A | * | 8/1996 | Lomas | 2/173 |
| 5,724,965 A | | 3/1998 | Handke et al. | |
| 6,119,694 A | | 9/2000 | Correa et al. | |
| 6,192,886 B1 | * | 2/2001 | Rudolph | 128/207.13 |
| 6,269,814 B1 | | 8/2001 | Blaszczykiewicz et al. | |
| 6,422,238 B1 | | 7/2002 | Lithgow | |
| 6,470,886 B1 | * | 10/2002 | Jestrabek-Hart | 128/207.11 |
| 6,494,207 B1 | * | 12/2002 | Kwok | 128/207.11 |

FOREIGN PATENT DOCUMENTS

AU 667006 10/1995

* cited by examiner

Primary Examiner—Henry Bennett
Assistant Examiner—Mital Patel
(74) Attorney, Agent, or Firm—Michael W. Haas

(57) ABSTRACT

A universally fitting headgear that is readily adjustable to a variety of different sized patients and that couples a patient interface device to an airway of the patient. The headgear includes a headpiece that fits on the user's heal in a cap-like fashion. The circumference of the headpiece is adjustable so that a single sized headgear can be fit to a number of different sized patient's. The headpiece includes adjustment straps which adjustably connect to each other on the sides of the patient's head. The headpiece further includes connecting straps to adjustably connecting the headgear to a patient interface device, such as a gas delivery mask. The headgear of the present invention fits a wide range of head sizes and shapes, is easy to use, and provides increased stability.

30 Claims, 7 Drawing Sheets

UNIVERSAL FITTING HEADGEAR

CROSS-REFERENCE TO RELATED APPLICATIONS

The application claims priority under 35 U.S.C. § 119(e) from U.S. provisional patent application No. 60/346,163 filed Nov. 7, 2001, the contents of which are incorporated herein by reference.

BACKGROUND OF THE INVENTION

1. Field of the Invention

The present invention generally relates to an adjustable headgear, and, more particularly, to an adjustable headgear having a universal fitting cap for affixing a gas delivery mask to a patient, and to a system for supplying a flow of gas to a patient that incorporates such an adjustable headgear.

2. Description of the Related Art

There are numerous situations where it is necessary or desirable to deliver a flow of breathing gas, non-invasively, to the airway of a patient, i.e., without intubating the patient or surgically inserting a trachea tube in their esophagus For example, it is known to ventilate a patient using a technique known as non-invasive ventilation. It is also known to deliver continuous positive airway pressure (CPAP) or variable airway pressure, which varies with the patient's respiratory cycle or with the patient's condition, to treat a medical disorder, such as sleep apnea syndrome, in particular, obstructive sleep apnea (OSA), or congestive heart failure.

Non-invasive ventilation and pressure support therapies involve the selective placement of a patient interface device, which is typically a nasal mask, a nasal/oral mask, or a full face mask, on the face of a patient. The patient interface device communicates the flow of breathing gas from the ventilator or pressure support device with the airway of the patient, so that the therapeutic flow of breathing gas can be delivered from the pressure/flow generating device to the airway of the patient. It is known to maintain such interface devices on the face of a wearer by a headgear having upper and lower straps, each having opposite ends threaded through connecting elements provided on the opposite sides and top of the interface device, such as a mask. Because such masks are typically worn for an extended period of time, it is important that the headgear maintain the mask in a tight enough seal against a patient's face without discomfort.

One such headgear is disclosed in U.S. Pat. No. 5,517,986 ("the '986 patent"). The headgear includes a headpiece 12 adapted to fit the crown and back of a patient's head. Lower straps 30 and 32 provide a two-point connection with a gas delivery mask 40. See FIG. 1 of the '986 patent. Depending straps 18 and 20, depending from headpiece 12, are connected to and moveable relative to the lower straps. Additionally, a pair of upper straps 56 and 58 can be used to provide a four-point connection with the gas delivery mask if needed. See FIG. 7 of the '986 patent. While the headgear disclosed in the '986 patent is adjustable it lacks adjustability in the cross direction of the head.

SUMMARY OF THE INVENTION

Accordingly, the present invention provides a universally adjustable headgear that is readily adjustable to affix a patient interface device, such as a mask, to a patient to create an effective seal between a gas delivery mask and the patient. The present invention further provides an adjustable headgear which is comfortable on the patient and fits a wide range of head sizes.

The headgear of the present invention includes a headpiece or cap portion that is adjustable in the cross direction of the patient's head to control the circumference of the headpiece. The headpiece includes adjustment straps which adjustably connect to each other on the sides of the head. The headpiece further includes connecting straps to adjustably connect the headgear to a patient interface or gas delivery mask. The present invention further comprises an assembly including an adjustable headgear having a universal fitting cap and a gas delivery mask, and to a system for supplying a flow of gas to a patient that incorporates such an adjustable headgear. The headgear of the present invention fits a wide range of head sizes and shapes, is easy to use and provides increased stability.

These features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood only and not intended as a definition of the limits of the invention.

DETAILED DESCRIPTION OF THE PRESENTLY PREFERRED EMBODIMENTS OF THE INVENTION

Figure 1:
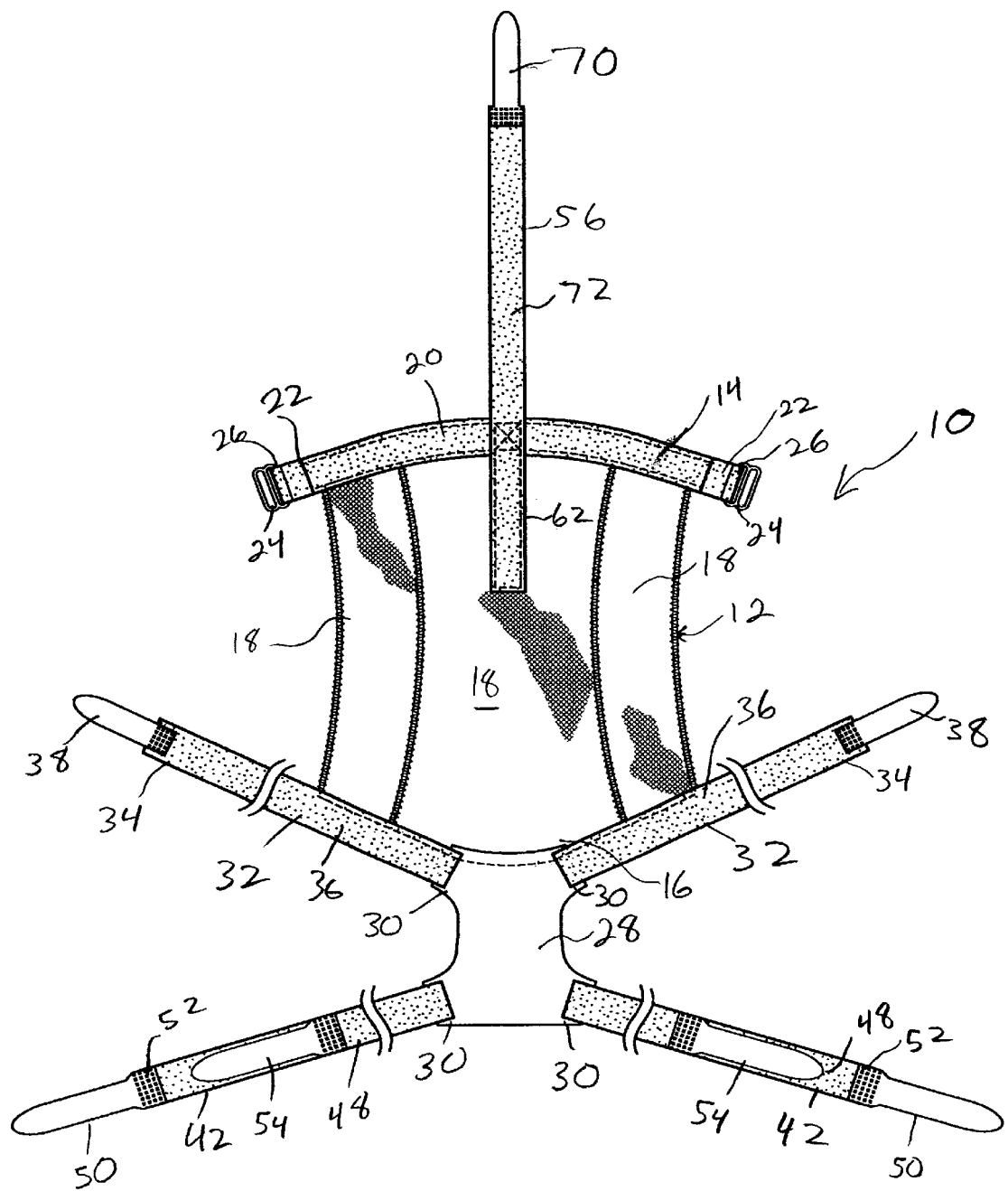
FIG. 1 is a plan view of the headgear according to the principles of the present invention.

FIGS. 1–5 illustrate an exemplary embodiment of an adjustable headgear 10 according to the principles to the present invention. Headgear 10 includes a cap or headpiece 12 having a front edge portion 14 positionable generally along the forehead of the patient and a rear edge portion 16 positionable generally along the rear portion of the patient's head. Headpiece 12 is preferably comprised of multiple panels 18 extending from the front edge portion 14 to the rear edge portion 16. Multiple panels are provided so that headpiece 12 covers a major portion of the cranium or skull, much like a cap or hat, to provide a substantially secure platform for mounting a patient interface device on a patient.

Panels 18 are preferably formed from a mesh-like material to allow for ventilation of the patient's head. Preferably, the mesh-like material is a NYLON LYCRA blend having sufficient elastic to adapted to different shaped heads. Of course, the present invention contemplates the panels 18 be made of other types of material as long as it provides sufficient elasticity, breathability and comfort. In addition, the number of panels defining headpiece 12 can be varied. For example, the present invention contemplates using a single panel as headpiece 12. However, in a preferred embodiment of the present invention, three panels 18 are used because this number of panels allows for maximum contouring of the headpiece to the patient's head with a minimal number of panels.

Adjustable headgear 10 further includes a front adjustment strap 20 attached to front edge portion 14 of mesh headpiece 12 and extending past either side of headpiece 12 to define front adjustment strap end portions 22. Front adjustment strap end portions 22 preferably have connecting elements 24 having elongated openings attached to their ends 26.

A rear joint piece 28 is attached to, and depends downwardly from, a central portion of the rear edge portion 16 of the headpiece at the upper edge of the rear joint piece, such that the rear joint piece is positionable along the lower rear portion of the patient's head. Rear joint piece 28 is generally rectangular or square in shape having four tab portions 30 extending from the four corners of the rectangle and is preferably made of an elastic lightweight air permeable material, such as LYCRA laminated foam. The present invention contemplates the rear joint piece 28 be made of other types of material such as NEOPRENE as long as it provides sufficient elasticity and comfort.

A pair of rear adjustment straps 32 are attached to and laterally extend from upper tabs portions 30. Each rear adjustment strap 32 is further attached to its respective tab portion 30, as well as a portion of the rear edge 16 of headpiece 12. Rear adjustment straps 32 extend past the headpiece forming rear adjustment strap end portions 34, which, when the headgear is properly positioned on a patient, extend above the patient's ears.

Front adjustment straps 20 and rear adjustment straps 32 preferably include a fastening system for adjustably and releasably connecting front adjustment strap end portion 22 and rear adjustment strap end portion 34 to one another. In the illustrated embodiment, the fastening system is a hook and loop fastener, such as VELCRO®. More specifically, in this embodiment, the exterior of the rear adjustment straps 32 includes a loop fastener portion 36. A corresponding hook fastener tab portion 38 is attached to each rear adjustment strap end portion 34. Thus, each rear adjustment strap 32 may be threaded through the elongated opening of the connecting element 24 of the front adjustment strap end portion 22 and then bent back on itself to adhere the hook fastener tab portion 38 via the exterior loop fastener portion 36 of the rear adjustment strap 32. Fastening front adjustment straps 20 and rear adjustment straps 32 together in this manner forms headpiece 12 into a cap-like formation that substantially covers the upper portion of the patient's head. In addition, an adjustment slot 40 is formed between the side edges of the headpiece 12 and the adjustment straps 20, 32 when connected, the size of which is controlled by the adjustable connection of the adjustment straps 20, 32.

It can be appreciated that the circumference of the cap-like structure can be adjusted based on the length of hook fastener tab portion 38 and/or rear adjustment strap end portion 34 that is inserted through the elongated opening of the connecting element 24. It is to be understood that the configuration of the fastening system can be reversed from that shown in the figures. For example, connecting element 24 can be provided on rear adjustment strap 32 and the hook and loop fasteners can be provided on front adjustment strap end portion 22. It is to be further understood that the present invention contemplates fastening techniques, other than the hook and loop system shown in the figures and described above. For example, one or more snaps can be provided along the exposed surface of the front and/or rear adjustment strap to provide attachment points between these two straps.

Figure 2:
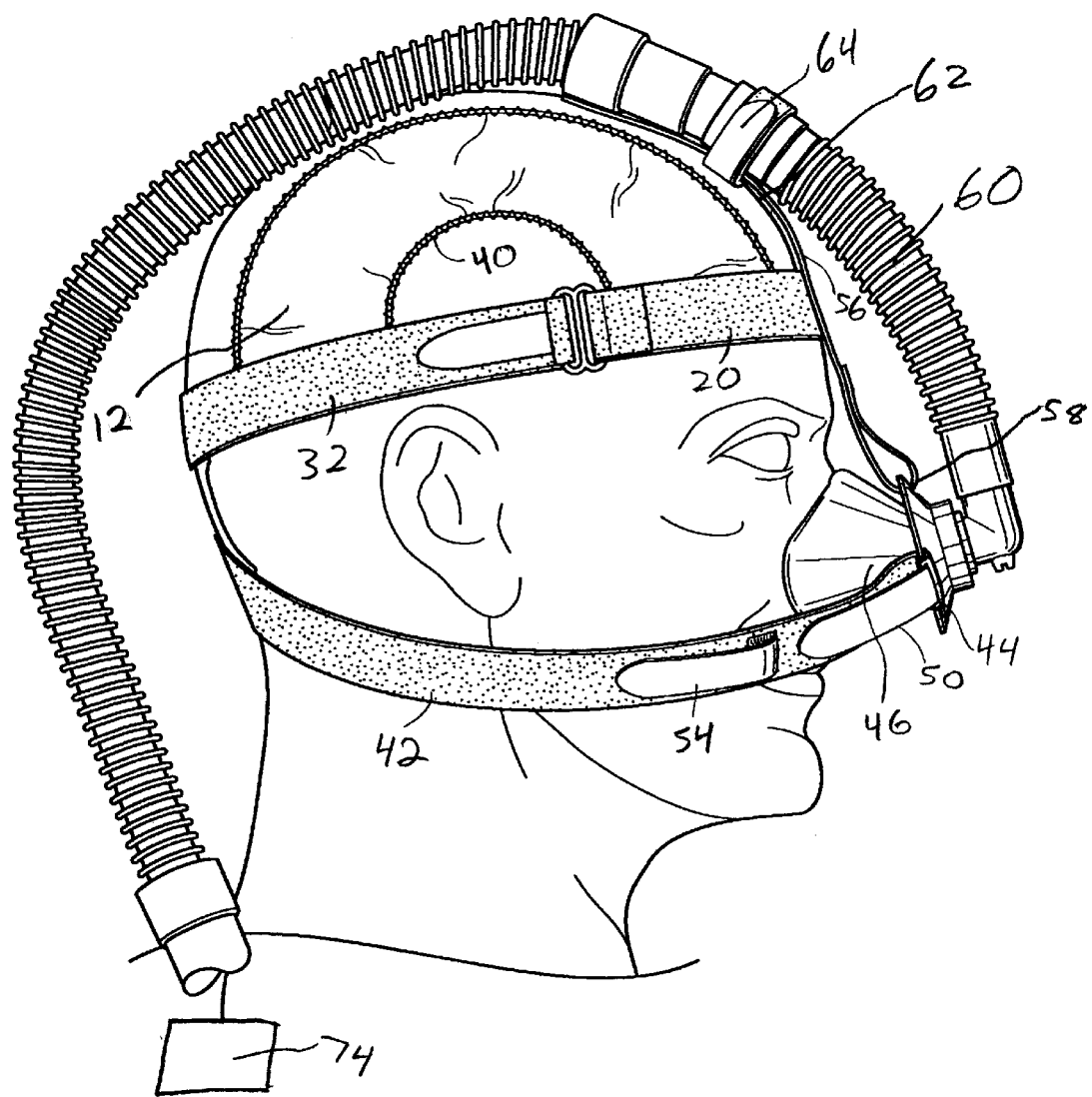
FIG. 2 is a side view and FIG. 3 is a front view of a patient wearing the headgear of FIG. 1 and a nasal mask.
Figure 3:
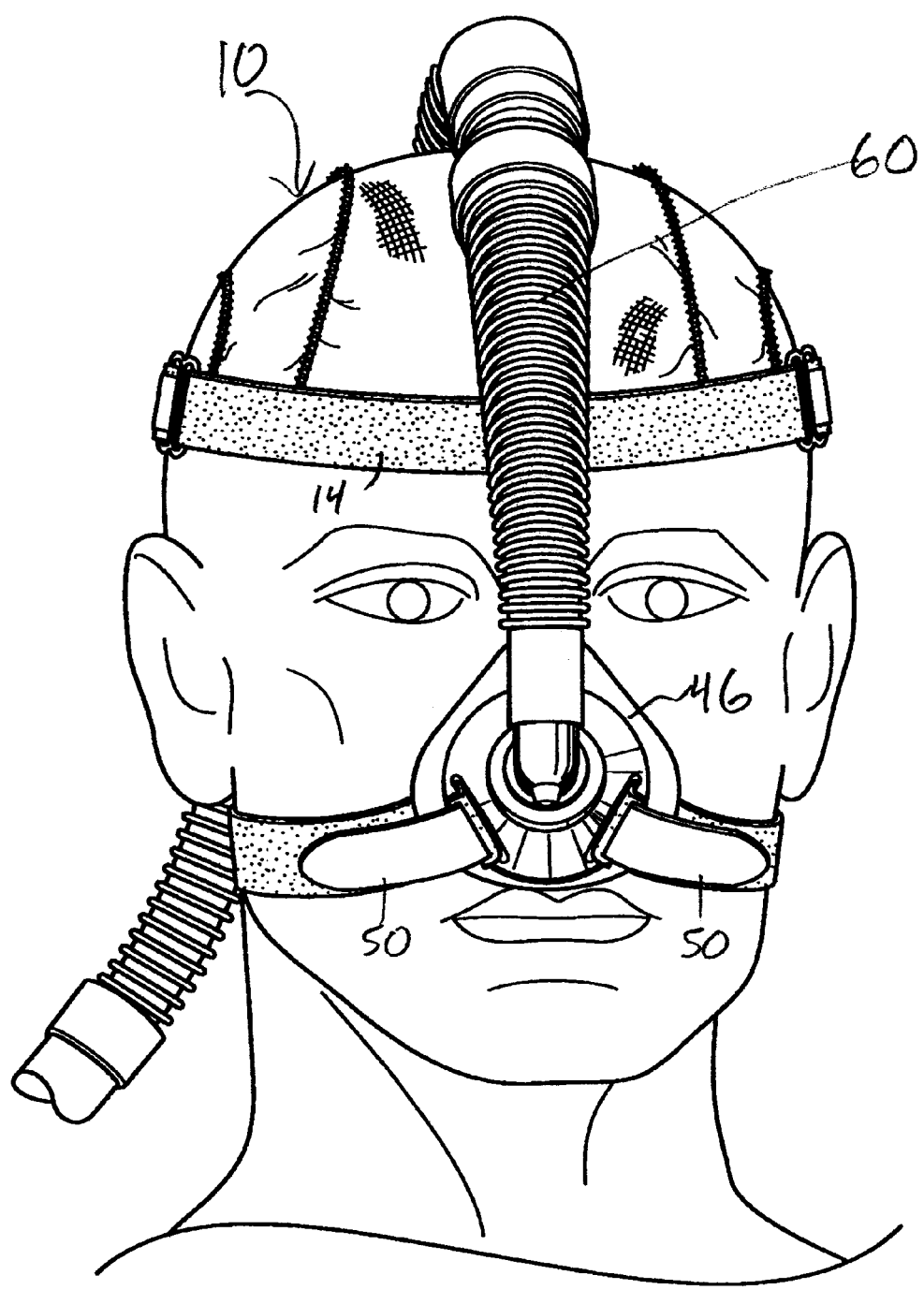
Figure 4:
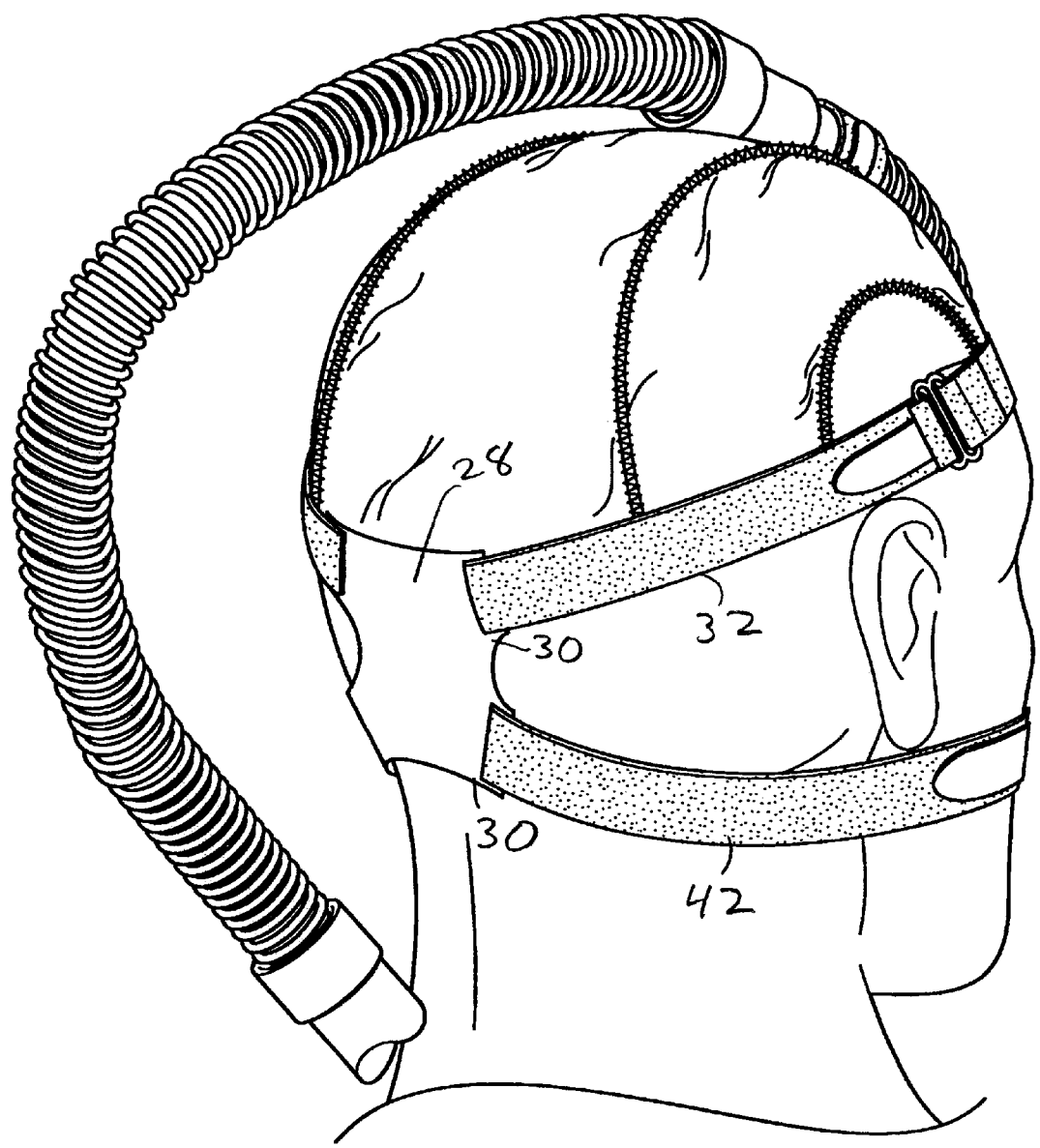
FIG. 4 is a rear perspective rear view of a patient wearing the headgear of FIG. 1.
Figure 5:
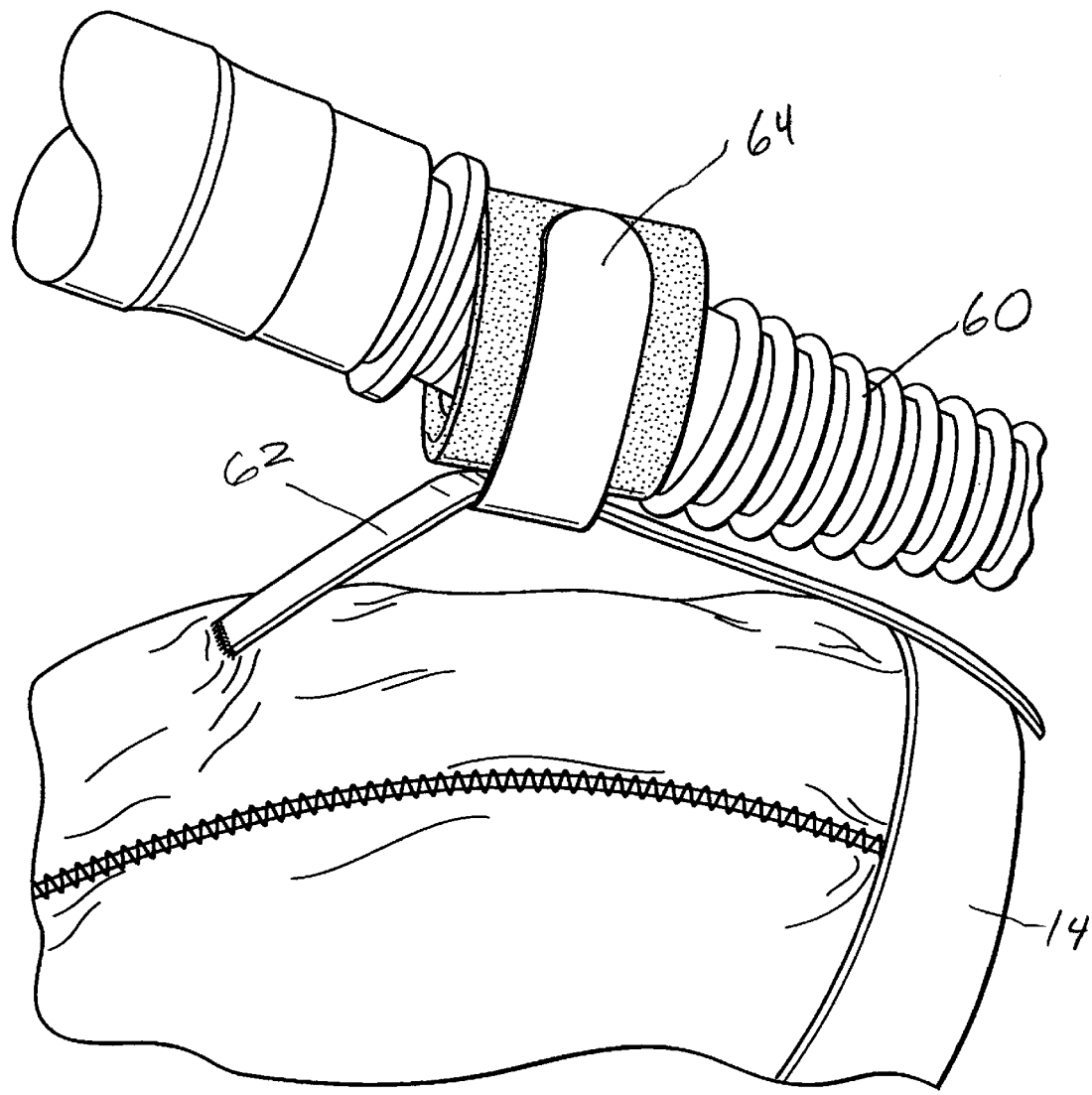
FIG. 5 is a detailed view of an optional conduit connection for use with the headgear of FIG. 1.

Headgear 10 further includes a pair of lower connecting straps 42 attached to the tab portions 30 on the lower edge of rear joint piece 28. Each lower connecting strap 42 extends forwardly, from the lower head of the patient, beneath the patient's ear, and is connectable to the side connecting elements 44 of a patient interface device 46, which, in the illustrated embodiment shown in FIGS. 2 and 3 is a nasal gas delivery mask.

Like rear adjustment straps 32, lower connecting straps 42 preferably include a fastening system for securing the lower connecting straps to the patient interface device. In the illustrated preferred embodiment, the fastening system is a hook and loop system that includes a loop fastener portion 48 disposed on an exterior of lower connecting straps 42 and a hook fastener tab portion 50 attached to each end portion 52 of lower connecting straps 42. Thus, each lower connecting strap 42 may be threaded through a connecting element 44 of patient interface device 46 and then bent back on itself to adhere hook fastener tab portion 50 to exterior loop fastener portion 48 of lower connecting strap 42 for adjustment.

Preferably, each lower connecting strap 42 includes at least one intermediary hook fastener tab portions 54 in addition to the hook fastener tab portions 50 attached to each end portion 52. Intermediary hook fastener tab portions 54 allow one size headgear 10 to fit a range of head sizes. When fitting headgear 10 on a smaller size head, intermediary hook fastener tab portion 54 on each lower connecting strap 42 (as well as the end hook fastener end portion 52) is threaded through connecting element 44 of patient interface device 46. Each intermediary hook fastener portion 54 is folded back on itself over the connecting element 44 to secure the mask 46 to the headgear 10. When in this configuration, each hook fastener tab portion 50 attached to each end portion 52 is also folded back on itself to secure to the exterior loop fastener portion 48 of each lower connecting strap 42 and prevent it from flapping in the patient's face. Alternatively, the extra length of end portions 52, including tab portion 50 can removed, for example, by cutting the excess length off with scissors. Similarly, intermediary hook fastener tab portion 54 can also be removed if not being used.

At least one upper connecting strap 56 extends from the front adjustment strap 14 across the patient's forehead to provide attachment to patient interface device 46. Upper connecting strap 56 preferably includes at least one hook fastener tab portion 70 attached to an end portion of the strap. Upper connecting strap 56 is threaded through a connecting element 58 of patient interface device 46 and then bent back on itself to attach hook fastener tab portion 70 to exterior loop fastener portion 72. In one embodiment, providing a three-point headgear, a single upper connecting strap 56 extends from the center of the front adjustment strap 20 and is securable to the mask 46 through an upper connecting element 58, such as an elongated opening, on the patient interface device of corresponding structure.

Figure 6:
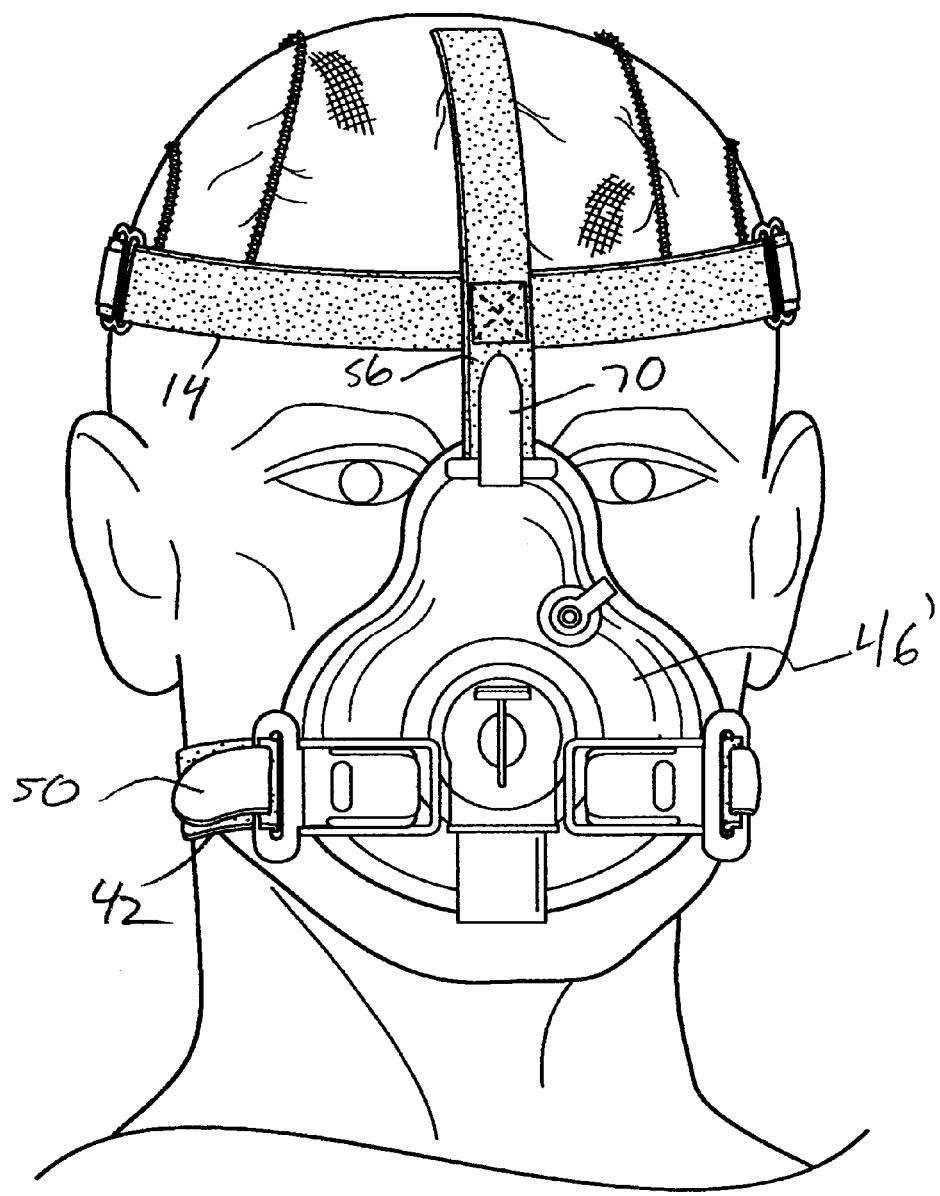
FIG. 6 is a front view of a patient wearing the headgear of FIG. 1 and a nasal/oral mask.

FIGS. 1–5 illustrates connection with a nasal mask 46 of the type disclosed in U.S. Des. Pat. No. D448,473 and in U.S. patent application Ser. Nos. 09/310,548 and 09/865,327 the contents of which are incorporated by reference herein. FIG. 6 illustrates connection with a nasal/oral face mask 46' of the type disclosed in U.S. patent application Ser. No. 29/142,895, the contents of which are also incorporated by reference herein. It is to be understood, however, that the type of patient interface device that can be attached to the patient by the headgear of the present invention is not intended to be limited to these specific devices.

In the mask of the type shown in FIG. 1–5, a conduit 60 extends upwardly from the mask and above the head of a patient. It is desirable to anchor the conduit for stability, i.e., to prevent the conduit from tugging on the mask and possibly dislodging it, and to prevent the conduit from interfering with the patient or the patient's bed partner. For these reasons, headgear 10 also preferably includes a belt loop type loop connection 62 (FIG. 5) formed by the attachment of upper connecting strap 56 to headpiece 12. A loop of material 64 surrounding the conduit having a hook and loop type fastening attachment is threaded through loop connection 62 to anchor conduit 60 to headgear 10.

Figure 7:
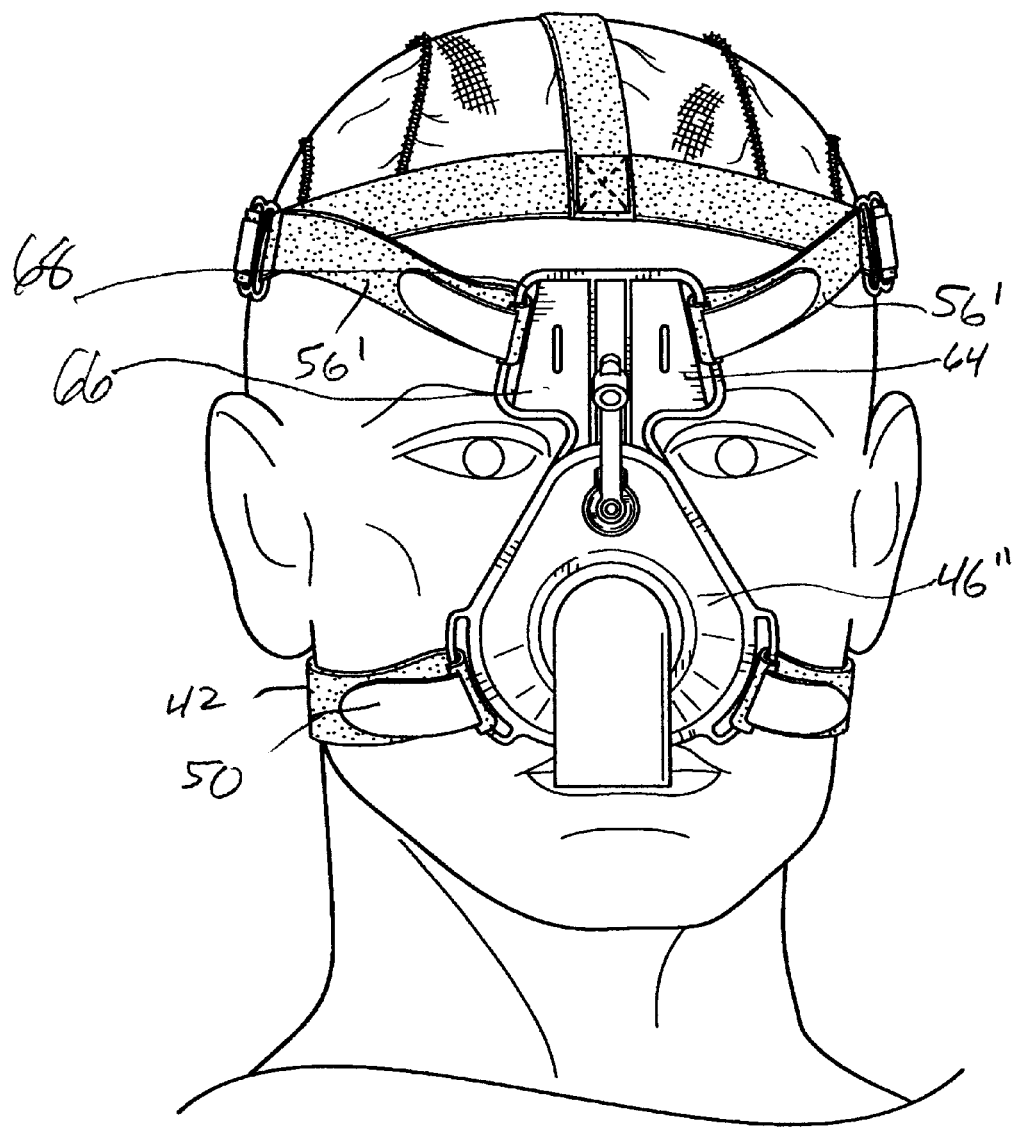
FIG. 7 is a front view of a patient wearing an alternative embodiment of a headgear with a nasal mask.

In another embodiment, a four-point patient interface device 46" is attached to the patient by headgear 10'. The phrase "four-point" refers to the number of locations on the patient interface that attaches to the headgear. In this embodiment, a pair of upper connecting straps 56' extend towards patient interface device 46" from the respective end portions of the front adjustment strap 20 and are used in conjunction with a forehead support assembly 64 of patient interface device 46" of the type shown in FIG. 7. This type of mask is described and/or shown, for example, in U.S. Des. Pat. No. D441,860 and U.S. patent application Ser. No. 09/362,402, the contents of which are incorporated by reference herein. Forehead support assembly 64 of the gas delivery mask comprises a soft pad (not illustrated) adapted to engage the forehead of the patient. The pad is secured to a plate 66 which includes elongated openings 68 through which the upper connecting straps 56' are threaded.

Like rear adjustment straps 32 and lower connecting straps 42, upper connecting strap(s) 56, 56' include a fastening system for securing an end of the strap to the patient interface device. As with the other straps, in a preferred embodiment of the present invention, this fastening system is a hook and loop fastening system that includes a hook and loop fastener. Thus, each upper connecting strap 56, 56' may be threaded through an elongated opening or connecting element 58, 68 of the gas delivery mask and then bent back on itself to attach hook fastener tab portion 70 to exterior loop fastener portion 72 of upper connecting strap 56, 56'. Also, the adjustment and connecting straps are all formed of an elastic material to provide for adjustment. Of course, the present invention contemplates the adjustment and connecting straps can use other forms of adjustment and connection other than hook and loop fasteners such as snaps or buckles. It should also be apparent that the other one of the hook and loop fastener component described above could be substituted for the component disclosed.

Patient interface device 46, 46', and 46" communicates a flow of breathing gas between the patient's airway and pressure generating device 74, such as a ventilator, CPAP device, or variable pressure device, e.g., a BiPAP® device manufactured and distributed by Respironics, Inc. of Pittsburgh, Pa., in which the pressure provided to the patient varies with the patient's respiratory cycle so that a higher pressure is delivered during inspiration than during expiration. Communicating a flow of breathing gas between the patient's airway and a pressure generating device 74 includes delivering a flow of breathing gas to the patient from the pressure generating device and exhausting a flow of gas from the patient to ambient atmosphere.

The system for delivering a breathing gas to a patient according to the present invention comprises (1) a pressure or gas flow generating device 74 that produces a flow of gas, (2) conduit 60 having a first end portion, operatively coupled to the gas flow generating device 74 and a second end portion, wherein the conduit 60 carries the flow of gas from the gas flow generating device 74 during operation of the system, (3) a patient interface device, such as gas delivery mask 46, 46', 46" coupled to the second end portion of conduit 60, and (4) an adjustable headgear 10 as described above that secures the patient interface device to the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An adjustable headgear comprising:
   a headpiece adapted to fit over a portion of a patient's head, the headpiece having a front edge portion positionable along a front portion of such a patient's head and a rear edge portion positionable along a rear portion of such a patient's head;
   a front adjustment strap attached to the front edge portion of the headpiece;
   a rear adjustment strap attached to the rear edge portion of the head piece, wherein the front adjustment strap and the rear adjustment strap are connectable together and adjustable to adjust the headpiece to fit a patient's head, wherein the headpiece, the front adjustment strap and the rear adjustment strap define a cap that fits over such a patient head, the cap having a perimeter that extends around a circumference of a patient's head, and wherein adjustment of the front adjustment strap with respect to the rear adjustment strap controls a circumference of the perimeter of the cap;
   a rear joint piece attached to and extending from the rear edge portion of the headpiece; and
   a lower connecting strap attached to the rear joint piece and adapted to releasably connect the headgear to a patient interface device.

2. The adjustable headgear of claim 1, further comprising a first upper connecting strap attached to the front edge portion of the headpiece and adapted to connect the headgear to the patient interface device.

3. The adjustable headgear of claim 2, further comprising a second upper connecting strap attached to the front edge portion of the headpiece and adapted to connect the headgear to the patient interface device.

4. The adjustable headgear of claim 2, wherein the upper and the lower connecting straps each include a fastening system adapted to adjustably and releasably connect the headgear to the patient interface device.

5. The adjustable headgear of claim 4, wherein the fastening system on each upper and lower connecting strap includes a loop fastener portion on the exterior surface of the upper and the lower connecting straps, and a hook tab portion disposed at an end portion of the upper and the lower connecting straps, wherein each hook tab portion is adapted for threading through a connecting element of the patient interface device and securing to the loop fastener portion.

6. The adjustable headgear of claim 1, wherein the front adjustment strap and the rear adjustment strap each include a fastening system adapted, to adjustably connect the front adjustment strap to the rear adjustment strap.

7. The adjustable headgear of claim 6, wherein the fastening system on the front adjustment strap and the rear adjustment strap includes (1) a connecting element disposed on one of the front adjustment strap and the rear adjustment strap and (2) a loop fastener portion and a first hook tab portion disposed on a remaining other of the front adjustment strap and the rear adjustment strap, wherein the loop fastener portion is disposed on an exterior surface of the front or the rear adjustment strap, wherein the first hook tab portion is disposed at a first location on the front or the rear adjustment strap, and wherein each hook tab portion is adapted for threading through the connecting element and securing to the loop fastener portion.

8. The adjustable headgear of claim 1, further comprising a second hook tab portion disposed at a second location on the front or the rear adjustment strap.

9. The adjustable headgear of claim 1, further comprising a connection element attached to the headpiece or the front edge portion and adapted to releasably connect a conduit to the headgear.

10. An adjustable headgear and patient interface assembly comprising:
   a patient interface device adapted to fit over a portion of the face of a patient and having connector elements on opposite sides thereof; and
   an adjustable headgear comprising:
      a headpiece adapted to fit over a portion of a patient's head, the headpiece having a front edge portion positionable along a front portion of such a patient's head and a rear edge portion positionable along a rear portion of such a patient's head;
      a front adjustment strap attached to the front edge portion of the headpiece;
      a rear adjustment strap attached to the rear edge portion of the head piece, wherein the front adjustment strap and the rear adjustment strap are connectable together and adjustable to adjust the headpiece to fit a patient's head, wherein the headpiece, the front adjustment strap, and the rear adjustment strap define a cap that fits over such a patient head, the cap having a perimeter that extends around a circumference of a patient's head, and wherein adjustment of the front adjustment strap with respect to the rear adjustment strap controls a circumference of the perimeter of the cap;
      a rear joint piece attached to and extending from the rear edge portion of the headpiece; and
      a lower connecting strap attached to the rear joint piece and adapted to releasably connect the headgear to the patient interface device.

11. The assembly of claim 10, further comprising a first upper connecting strap attached to the front edge portion of the headpiece and adapted to connect the headgear to the patient interface device.

12. The assembly of claim 11, further comprising a second upper connecting strap attached to the front edge portion of the headpiece and adapted to connect the headgear to the patient interface device.

13. The assembly of claim 11, wherein the upper and the lower connecting straps each include a fastening system adapted to adjustably and releasably connect the headgear to the patient interface device.

14. The assembly of claim 13, wherein the fastening system on each upper and lower connecting strap includes a loop fastener portion on the exterior surface of the upper and the lower connecting straps, and a hook tab portion disposed at an end portion of the upper and the lower connecting straps, wherein each hook tab portion is adapted for threading through a connecting element of the patient interface device and securing to the loop fastener portion.

15. The assembly of claim 10, wherein the front adjustment strap and the rear adjustment strap each include a fastening system adapted to adjustably connect the front adjustment strap to the rear adjustment strap.

16. The assembly of claim 15, wherein the fastening system on the front adjustment strap and the rear adjustment strap includes (1) a connecting element disposed on one of the front adjustment strap and the rear adjustment strap and (2) a loop fastener portion and a first hook tab portion disposed on a remaining other of the front adjustment strap and the rear adjustment strap, wherein the loop fastener portion is disposed on an exterior surface of the front or the rear adjustment strap, wherein the first hook tab portion is disposed at a first location on the front or the rear adjustment strap, and wherein each hook tab portion is adapted for threading through the connecting element and securing to the loop fastener portion.

17. The assembly of claim 16, further comprising a second hook tab portion disposed at a second location on the front or the rear adjustment strap.

18. The assembly of claim 10, further comprising a connection element attached to the headpiece or the front edge portion and adapted to releasably connect a conduit to the headgear.

19. The assembly of claim 10, wherein the patient interface device is a nasal mask or nasal/oral mask.

20. A system for delivering a breathing gas to a patient comprising:
   gas flow generating device that produces a flow of gas;
   a conduit having a first end portion operatively coupled to the gas flow generating device and a second end portion, wherein the conduit carries the flow of gas from the gas flow generating device during operation of the system;
   a patient interface device coupled to the second end portion of the conduit, the mask comprising having connector elements on opposite sides thereof; and
   an adjustable headgear comprising:
      a headpiece adapted to fit over a portion of a patient's head, the headpiece having a front edge portion positionable along a front portion of such a patient's head and a rear edge portion positionable along a rear portion of such a patient's head;
      a front adjustment strap attached to the front edge portion of the headpiece;
      a rear adjustment strap attached to the rear edge portion of the head piece, wherein the front adjustment strap and the rear adjustment strap are connectable together and adjustable to adjust the headpiece to fit a patient's head, wherein the headpiece, the front adjustment strap, and the rear adjustment strap define a cap that fits over such a patient head, the cap having a perimeter that extends around a circumference of a patient's head, and wherein adjustment of the front adjustment strap with respect to the rear adjustment strap controls a circumference of the perimeter of the cap;
      a rear joint piece attached to and extending from the rear edge portion of the headpiece; and
      a lower connecting strap attached to the rear joint piece and adapted to releasably connect the headgear to a patient interface device.

21. The system of claim 20, further comprising a first upper connecting strap attached to the front edge portion of the headpiece and adapted to connect the headgear to the patient interface device.

22. The system of claim 21, further comprising a second upper connecting strap attached to the front edge portion of the headpiece and adapted to connect the headgear to the patient interface device.

23. The system of claim 21, wherein the upper and the lower connecting straps each include a fastening system adapted to adjustably and releasably connect the headgear to the patient interface device.

24. The system of claim 23, wherein the fastening system on each upper and lower connecting strap includes a loop fastener portion on the exterior surface of the upper and the lower connecting straps, and a hook tab portion disposed at an end portion of the upper and the lower connecting straps, wherein each hook tab portion is adapted for threading through a connecting element of the patient interface device and securing to the loop fastener portion.

25. The system of claim 20, wherein the front adjustment strap and the rear adjustment strap each include a fastening system adapted to adjustably connect the front adjustment strap to the rear adjustment strap.

26. The system of claim 25, wherein the fastening system on the front adjustment strap and the rear adjustment strap includes (1) a connecting element disposed on one of the front adjustment strap and the rear adjustment strap and (2) a loop fastener portion and a first hook tab portion disposed on a remaining other of the front adjustment strap and the rear adjustment strap, wherein the loop fastener portion is disposed on an exterior surface of the front or the rear adjustment strap, wherein the first hook tab portion is disposed at a first location on the front or the rear adjustment strap, and wherein each hook tab portion is adapted for threading through the connecting element and securing to the loop fastener portion.

27. The system of claim 26, further comprising a second hook tab portion disposed at a second location on the front or the rear adjustment strap.

28. The system of claim 20, further comprising a connection element attached to the headpiece or the front edge portion and adapted to releasably connect a conduit to the headgear.

29. The system of claim 20, wherein the patient interface device is a nasal mask or nasal/oral mask.

30. An adjustable headgear comprising:

headpiece having a front edge portion positionable along a front portion of such a patient's head and a rear edge portion positionable along a rear portion of such a patient's head;

a front adjustment strap attached to the front edge portion of the headpiece;

a rear adjustment strap attached to the rear edge portion of the head piece, wherein the front adjustment strap and the rear adjustment strap are connectable together and adjustable to adjust the headpiece to fit a patient's head, wherein the headpiece, the front adjustment strap and the rear adjustment strap define a cap that is sized, configured and arranged so as to encircle a patient's cranium above ear-level and cover a majority of such a patient's head responsive to the headgear being donned by the patient, wherein the cap has a perimeter that extends around a circumference of a patient's head, and wherein adjustment of the front adjustment strap with respect to the rear adjustment strap controls a circumference of the perimeter of the cap; and a lower connecting strap having a first end operatively attached to the a rear adjustment strap and a second end adapted to releasably connect the headgear to a patient interface device.

* * * * *